(12) United States Patent
Studier

(10) Patent No.: US 7,759,109 B2
(45) Date of Patent: Jul. 20, 2010

(54) HIGH DENSITY GROWTH OF T7 EXPRESSION STRAINS WITH AUTO-INDUCTION OPTION

(75) Inventor: F. William Studier, Stony Brook, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

(21) Appl. No.: 12/062,565

(22) Filed: Apr. 4, 2008

(65) Prior Publication Data

US 2008/0187985 A1    Aug. 7, 2008

Related U.S. Application Data

(63) Continuation of application No. 11/741,282, filed on Apr. 27, 2007, which is a continuation-in-part of application No. 10/675,936, filed on Sep. 30, 2003, now Pat. No. 7,560,264.

(60) Provisional application No. 60/455,032, filed on Mar. 14, 2003.

(51) Int. Cl.
    *C12N 1/20* (2006.01)
    *C12N 1/38* (2006.01)
(52) U.S. Cl. .................................. 435/253.6; 435/244
(58) Field of Classification Search ........................ None
    See application file for complete search history.

(56) References Cited

OTHER PUBLICATIONS

Studier, "Protein Production by Auto-Induction in High-Density Shaking Cultures", *Protein Expression & Purification*, 41, 207-234 (2005).
Dubendorff, et al., "Controlling Basal Expression in an Inducible T7 Expression System by Blocking the Target T7 Promoter with *lac* Represstor", *J. Mol. Biol.*, 219, 45-59 (1991).
Studier, et al., "Use of T7 RNA Polymerase to Direct Expression of Cloned Genes", *Methods in Enzymology*, 185, 60-89 (1990).
Studier, et al., "Use of Bacteriophage T7 RNA Polymerase to Direct Selective High-Level Expression of Cloned Genes", *J Mol. Biol.*, 189, 113-130 (1986).
Grossman, et al., "Spontaneous cAMP-dependent Derepression of Gene Expression in Stationary Phase Plays a Role in Recombinant Expression Instability", *Gene*, 209, 95-103 (1998).
Fischer, et al., "The General Stress Sigma Factor $\sigma^S$ of *Escherichia coli* Is Induced During Diauxic Shift from Glucose to Lactose", *J. of Bacteriology*, 180, No. 23, 6203-6206 (1998).
Kapralek, et al., "Fermentation Conditions for High-Level Expression of the tac-Promoter-Controlled Calf Prochymosin cDNA in *Escherichia coli*HB101", *Biotech. And Bioeng.*, 37, 71-79 (1991).
Kimata, et al., "cAMP Receptor Protein-cAMP Plays a Crucial Role in Glucose-Lactose Diauxie by Activating the Major Glucose Transporter Gene in *Escherichia coli*", *Proc. Natl. Acad. Sci.*, 94, 12914-12919 (1997).

Tyler, et al., "Auto-Induction Medium for the Production of [U-$^{15}$N]- and [U-$^{13}$C, U-$^{15}$N]-labeled Tyler, et al., "Auto-Induction Medium for the Production of [U-$^{15}$N]- and [U-$^{13}$C, U-$^{15}$N]-labeled Proteins for NMR Screening and Structure Determination", Protein Expression & Purification, 40, 268-278 (2005).Proteins for NMR Screening and Structure Determination", *Protein Expression & Purification*, 40, 268-278 (2005).
Sreenath, et al., "Protocols for Production of Selenomethionine-Labeled Proteins in 2-L Polyethylene Terephthalate Bottles Using Auto-Induction Medium", *Protein Expression & Purification*,40, 256-267 (2005).
Goulding et al., "Protein Production in *Escherichia coli* for Structural Studies by X-ray Crystallography", *J of Structural Biology*, 142, 133-143 (2003).
Grabski, et al., "The Overnight Express Autoinduction System: High-density Cell Growth and Protein Expression While You Sleep", *Nature Methods*, 2, 233-235 (2005).
Berrow, et al., "Recombinant Protein Expression and Solubility Screening in *Escherichia coli*: A Comparative Study", *Acta Cryst.*, D62, 1218-1226 (2006).
Menzella, et al., "Novel *Escherichia coli* Strain Allows Efficient Recombinant Protein Production Using Lactose as Inducer", *Biotech and Bioeng.*, 82, 809-817 (2003).
Mehlin, et al., "Heterologous Expression of Proteins from *Plasmodium falciparum*: Results from 1000 Genes", *Mol. & Biochem. Parasitology*, 148, 144-160 (2006).
Bashiri, et al., "Expression, Purification and Crystallization of Native and Selenomethionine Labeled *Mycobacterium tuberculosis* FGD1 (Rv0407) Using a *Mycobacterium smegmatis* Expression System", *Protein Expression & Purification*, 54, 38-44 (2007).
Blommel, et al., "Enhanced Bacterial Protein Expression During Auto-Induction Obtained by Alteration of Lac Repressor Dosage and Medium Composition", *Biotechnol.Prog.*, 23, 585-598 (2007).
Hoffman,et al., "Lactose Fed-Batch Overexpression of Recombinant Metalloproteins in *Escherichia coli* B121(DE3): Process Control Yielding High Levels of Metal-Incorporated, Soluble Protein", *Protein Expression & Purification*, 6, 646-654 (1995).
Neubauer, et al., "Maximizing the Expression of a Recombinant Gene in *Escherichia coli* by Manipulation of Induction Time Using Lactose as Inducer", *Appl. Microbiol. Biotechnol.*, 36, 739-744 (1992).

*Primary Examiner*—Nancy Vogel
(74) *Attorney, Agent, or Firm*—Dorene M. Price

(57) ABSTRACT

A bacterial growth medium for promoting auto-induction of transcription of cloned DNA in cultures of bacterial cells grown batchwise is disclosed. The transcription is under the control of a lac repressor. Also disclosed is a bacterial growth medium for improving the production of a selenomethionine-containing protein or polypeptide in a bacterial cell, the protein or polypeptide being produced by recombinant DNA techniques from a lac or T7lac promoter, the bacterial cell encoding a vitamin B12-dependent homocysteine methylase. Finally, disclosed is a bacterial growth medium for suppressing auto-induction of expression in cultures of bacterial cells grown batchwise, said transcription being under the control of lac repressor.

15 Claims, No Drawings

HIGH DENSITY GROWTH OF T7 EXPRESSION STRAINS WITH AUTO-INDUCTION OPTION

PARENT CASE TEXT

This application is a continuation of U.S. application Ser. No. 11/741,282, filed Apr. 27, 2007, which is a continuation-in-part of U.S. application Ser. No. 10/675,936 filed Sep. 30, 2003, which application draws priority of U.S. Provisional Application No. 60/455,032, filed Mar. 14, 2003.

GOVERNMENT SUPPORT

This invention was made with Government support under contract number DE-AC02-98CH10886, awarded by the U.S. Department of Energy. The Government has certain rights in the invention.

BACKGROUND OF THE INVENTION

DNA sequencing projects have provided coding sequences for hundreds of thousands of proteins from organisms across the evolutionary spectrum. Recombinant DNA technology makes it possible to clone these coding sequences into expression vectors that can direct the production of the corresponding proteins in suitable host cells. The resulting proteins are widely useful, as objects of biochemical, biophysical, structural and functional studies for understanding basic biological processes, as enzymes to serve as research tools or produce valuable chemicals, as diagnostics, vaccines, therapeutics or targets for developing medically useful drugs, or for protein chips, to mention a few.

The T7 expression system comprises in vivo inducible expression, in T7 expression system host strains, of T7 RNA polymerase from a chromosomal copy of a cloned gene for the T7 RNA polymerase enzyme (gene 1 of bacteriophage T7), followed in turn by recognition and binding of a T7 promoter sequence contained in T7 expression vectors carried in the host strain, followed by intense transcription of any gene(s) cloned downstream of the T7 promoter sequence, and, where the cloned sequence is a protein coding sequence, subsequent translation of the transcripts. This recombinant gene expression system, originally developed in *Escherichia coli* and which has become the standard by which other prokaryotic expression systems are judged, has been adapted for use in other bacterial species including *Salmonella enteric serovar Typhimurium* (McKinney, J., et al. (2002) J. Bacteriology 184:6056-6059), *Pseudomonads* (Schweizer, H P (2001) Curr. Opin. Biotechnol. 12:439-445), *Rhodobacter capsulatus* (Drepper, T., et al. (2005) Biochem. Soc. Trans. 33:56-58), *Ralstonia eutropha* (Barnard, G. C., et al. (2004) Prot. Exp. & Purif. 38:264-271) and *Bacillus subtilis* (Conrad, B., et al. (1996) Mol. Gen. Genet. 250:230-236).

The inducible T7 expression system is highly effective and widely used to produce RNAs and proteins from cloned coding sequences in the bacterium *Escherichia coli* (Studier and Moffatt, *J. Mol. Biol.* 189: 113-130 (1986); Studier et al., *Methods in Enzymology* 185: 60-89 (1990); Novagen). The coding sequence for T7 RNA polymerase is typically present in the chromosome under control of the inducible lac or lacUV5 promoter in the chromosome of host cells such as BL21(DE3), B834(DE3) and HMS174(DE3), and derivatives of such cells such as ER2566 and ER 2833 (New England Biolabs). In another derivative strain, designated "BL21-AI" (Invitrogen), gene 1 is under the control of the arabinose-inducible araBAD promoter. In the absence of inducing compounds, transcription by the host cell RNA polymerase is blocked by the natural endogenous repressor. In the case of the lac promoter, it is the lac repressor and for the araBAD promoter, the product of the araC gene is the repressor.

The coding sequence for the desired RNA or protein (referred to as the target RNA or protein) is typically placed in a plasmid under control of a T7 promoter, that is, a promoter recognized specifically by T7 RNA polymerase. In the absence of an inducer for the lacUV5 promoter, little T7 RNA polymerase or target protein should be present and the cells should grow well. However, upon addition of an inducer, typically IPTG (isopropyl-β-D-thiogalactoside), T7 RNA polymerase will be made and will transcribe almost any DNA controlled by the T7 promoter. T7 RNA polymerase is so specific, active and processive that the amount of target RNA produced can be comparable to the amount of ribosomal RNA in a cell. Thus, large amounts of RNAs that are useful in themselves, such as ribozymes, can be produced. If the target RNA contains the coding sequence for a protein and appropriate translation initiation signals (such as the sequence upstream of the start codon for the T7 major capsid protein), target protein can be produced, often accumulating to become a substantial fraction of total cell protein. See also U.S. Pat. Nos. 4,952,496; 5,693,489; and 5,869,320, the contents of which are incorporated herein by reference.

In strains in which the T7 gene 1 (T7 RNA polymerase gene) is under control of the lac or lacUV5, IPTG has typically been used to induce expression of target proteins. Lactose will also cause induction and, being much cheaper than IPTG, may be preferable for large-scale production. Neubauer et al., *Appl. Microbiol. Biotechnol.* 36: 739-744 (1992) obtained induction by lactose with the same efficiency as with IPTG by careful monitoring of the glucose level in fermentation and by addition of lactose when the glucose was nearly depleted. Hoffman et al., *Protein Expression and Purification* 6: 646-654 (1995) used similar procedures to obtain comparable levels of protein synthesis with lactose or IPTG induction in a fermentor process.

A problem in using inducible T7 expression systems is that T7 RNA polymerase is so active that a small basal level can lead to a substantial expression of target protein even in the absence of added inducer. If the target protein is sufficiently toxic to the host cell, establishment of the target plasmid in the expression host may be difficult or impossible, or the expression strain may be unstable or accumulate mutations (Kelley et al., Gene 156: 33-36 (1995)). An effective means to reduce basal expression (and thereby increase the range and stability of target proteins that can be established and expressed) is to place the lac operator sequence (the binding site for lac repressor) just downstream of the start site of a T7 promoter, creating a T7lac promoter (Dubendorff and Studier, *J. Mol. Biol.* 219: 45-59 (1991)). Lac repressor bound at the operator sequence interferes with establishment of an elongation complex by T7 RNA polymerase at a T7lac promoter and substantially reduces the level of target mRNA produced. If sufficient lac repressor is present to saturate all of its binding sites in the cell, the basal level of target protein in uninduced cells is substantially reduced, but induction unblocks both the lacUV5 and T7lac promoters and leads to the typical high levels of expression. Thus, the T7lac promoter increases the convenience and applicability of the T7 system for expressing a wide range of proteins.

It was early noticed that growth of T7 expression cultures to saturation could cause problems, and Grossman et al., *Gene* 209: 95-103 (1998) showed that cultures growing in certain complex media induce the target protein to high levels upon approach to saturation even when the T7lac promoter was used. They pointed out that such unintended induction could be a problem in isolating and using strains that express proteins that are toxic to *E. coli*. They concluded that the known inducer lactose was not responsible for this effect, but that cyclic AMP is required, and they recommended using a mutant unable to make cyclic AMP as an expression host.

Although such basal level of expression from T7 expression vectors can be suppressed through use of the T7lac promoter in such vectors, this does not solve problems resulting from unintended induction of T7 expression strains when they are grown to saturation, which was noted by Grossman et al. (*Gene* 209: 95-103 (1998)). Grossman et al. showed that cultures growing in certain complex media induce the target protein to high levels upon approach to saturation even when the T7lac promoter was used. They pointed out that such unintended induction could be a problem in isolating and using strains that express proteins that are toxic to *E. coli*. In their work, they concluded that lactose had not been responsible for this effect, but that cyclic AMP was required, and they recommended using a mutant host strain that is unable to make cyclic AMP. They also found that addition of 1% glucose to late log phase cells prevented the unintended induction, and the Novagen web site references their paper and recommends adding 1% glucose to the medium to manage this problem.

Structural genomics is an area where multi-milligram amounts of many different proteins over a wide evolutionary range are required for determination of protein structures by X-ray crystallography or nuclear magnetic resonance (NMR). Fabrication of protein chips is another application where many different proteins are needed. Expressing cloned coding sequences in the T7 system is an efficient, widely used method for obtaining these proteins. Screening large numbers of clones for protein expression level and solubility makes it desirable to have procedures that can be applied to many clones in parallel, preferably using automation. The need to process many cultures in parallel dictates batchwise growth of cultures in small vessels such as culture tubes or multi-well plates such as the 24-, 96- or 384-well plates commonly available. A high level of protein production per volume of culture is also desirable. The needed multi-milligram amounts of pure protein could be produced in fermentors, but cultures grown batchwise in vessels aerated by shaking (a baffled flask on a rotary shaker, for example), bubbling air, or oxygen can typically produce this amount of protein in the T7 expression system in a liter or less of culture, allowing several cultures, each producing a different protein, to be grown and induced in parallel.

In trying to develop reliable procedures for growing and inducing protein synthesis in many cultures in parallel, a significant difficulty was to obtain all of the cultures in a comparable state of growth so that they could be induced simultaneously in parallel. Substantial effort was required to measure the cell density of each culture and add inducer at the proper time, even using a plate reader that could measure the densities of cultures in all of the different wells of a plate in a single reading. Even if comparable amounts of culture could be inoculated in each well, differences in lag time or growth rate typically generated situations where cultures in different wells would be ready for induction at substantially different times. If the entire plate was to be collected at once, cultures would also vary in the length of time in which they had been producing target protein, possibly making it difficult to choose a time when all had been induced to optimal levels without substantial overgrowth of some cultures by cells that had lost plasmid.

An obvious strategy was to grow the entire plate to saturation in a small volume of medium in each well, dilute by adding fresh medium, grow for an appropriate time (determined by previous testing or by direct measurement of cell densities), and add inducer to all wells at the same time. The hope was that all cultures in a plate would saturate at near enough to the same density and grow after dilution with similar enough kinetics that the culture-to-culture variation in density at the time of induction would be tolerable. However, in trying to implement this strategy, when certain lots of complex growth media were used, the problem described by Grossman et al. (1998) was encountered, namely, induction during the growth to saturation. Indeed, it was found that media made with a particular lot of N-Z-amine showed this induction behavior, whereas otherwise identical media made with a second lot from the same supplier did not. Unwanted induction at saturation would make it extremely difficult to obtain sufficient uniformity of growth to permit parallel manipulation of cultures expressing target proteins of different, usually unknown degrees of toxicity. Although addition of glucose could suppress this induction (Novagen), the saturated cultures could become very acid, which would limit the saturation density and again make it difficult to get uniform growth upon dilution. Screening different lots of N-Z-amine for those without the inducing behavior did not seem to be an attractive solution, as there was no guarantee that such lots would always be available. Thus, the approaches taken, leading to the present invention, were to determine causes of and ways to prevent unwanted induction and to develop means to promote desirable auto-induction of expression strains.

The ability to control the problem of sporadic, unwanted induction in complex media would represent a significant advance in the art. A systematic analysis of the components of both complex and defined media was undertaken. The goal was to define requirements for batchwise growth of T7 expression strains to high density under conditions suitable for growth and induction of many cultures in parallel, and, complementarily, to develop formulations that would reliably grow cultures of expression strains to saturation with little or no induction.

SUMMARY OF THE INVENTION

The present invention relates, in one aspect, to a method and growth media for promoting auto-induction of transcription of cloned DNA in cultures of bacterial cells grown batchwise, the transcription being under the control of a promoter whose activity can be induced by an exogenous inducer whose ability to induce said promoter is dependent on the metabolic state of said bacterial cells. Initially, a culture media is provided which includes: i) an inducer capable of inducing transcription from said promoter in said bacterial cells; and ii) a metabolite that prevents induction by said inducer, the concentration of said metabolite being adjusted so as to substantially preclude induction by said inducer in the early stages (early to mid-log phase) of growth of the bacterial culture, but such that said metabolite is depleted to a level that allows induction by said inducer at a later stage of growth (mid to late-log phase and prior to saturation). The culture medium is inoculated with a bacterial inoculum, the inoculum comprising bacterial cells containing cloned DNA, the transcription of which is induced by said inducer. The culture is then incubated under conditions appropriate for growth of the bacterial cells until such growth sufficiently depletes the metabolite such that auto-induction of transcription occurs, and where applicable the transcripts have been translated.

In a preferred embodiment, the present invention relates to promoting auto-induction of transcription of cloned gene 1 of bacteriophage T7 in batchwise-grown bacterial cells, which cloned gene is under the control of an inducible promoter and is stably propagated in the bacterial cells. A culture medium comprising an exogenous inducer which is capable of inducing transcription from the inducible promoter and one or more constituents that prevents induction by said inducer until such time as growth and division of the bacterial cells has depleted the one or more constituents of the culture medium to a level that permits induction by the inducer. The provided culture medium is inoculated with the bacterial cells, the culture is incubated under conditions for growth of the bacterial cells until the level of the one or more constituents has been depleted to a level permitting auto-induction of transcription of the cloned gene 1.

This embodiment of the present invention further includes incubating the culture to permit translation of the gene 1 transcripts into T7 RNA polymerase enzyme. The present invention also includes bacterial cells which are T7 expression strains, i.e., the cells contain a T7 expression plasmid in which a target gene is under the control of a T7 promoter (e.g., pET vectors (Novagen); Variflex vectors (Stratagene) and pRSET vectors (Invitrogen), etc.). The present invention further includes incubating the culture until such time as the T7 RNA polymerase enzyme has transcribed target genes under the control of a T7 promoter, and, further includes incubating the culture until such time as the latter transcripts are translated into protein. In general the preferred embodiment includes incubating the inoculated cultures until a saturating cell density is achieved.

In another aspect, the present invention relates to a method for improving the production of a selenomethionine-containing protein or polypeptide in a bacterial cell, the protein or polypeptide being produced by recombinant DNA techniques, the bacterial cell encoding a vitamin B12-dependent homocysteine methylase. The method for improving the production of this protein or polypeptide includes culturing the bacterial cell in a culture medium containing vitamin B12.

In another aspect, the invention relates to a method for suppressing transcription of cloned DNA in cultures of bacterial cells grown batchwise, said transcription being under the control of a promoter whose activity can be induced by an exogenous inducer whose ability to induce said promoter is dependent on the metabolic state of said bacterial cells. This aspect includes the steps of: a) providing a culture medium comprising a carbon source whose uptake and metabolism by said bacterial cells suppresses induction of transcription from said promoter; b) inoculating the culture medium with a bacterial inoculum, the inoculum comprising bacterial cells containing cloned DNA, the transcription of which is suppressed by the carbon source; and c) incubating the culture of step b), with shaking, under conditions appropriate for growth of the bacterial cells while suppressing transcription of the cloned DNA.

DETAILED DESCRIPTION OF THE INVENTION

1. Development of Non-Inducing Media

Well known media for growth of *E. coli* and production of target proteins with the T7 expression system include ZB, ZY (equivalent to LB), M9 or M9ZB, which contain various combinations of 1% of a tryptic digest of casein (such as tryptone or N-Z-amine AS), 0.5% yeast extract, 0.5% NaCl, or the components of M9 medium (Studier and Moffatt, *J. Mol. Biol.* 189: 113-130 (1986)). These were the starting components in the search for formulations that would allow batchwise growth to high cell densities with reproducible and reliable behavior relative to induction of protein expression in the T7 system. The *E. coli* strains used for testing growth and expression were primarily BL21 (DE3) or B834(DE3), alone or containing plasmids containing coding sequences under control of the T7lac promoter and the upstream translation initiation signals of the T7 major capsid protein.

The standard measure of growth was optical density at 600 nm (A600) after dilution in water to concentrations that gave readings below 0.25. Viability and stability of cultures grown under different conditions were tested by plating, usually on agar plates containing ZB. A standard configuration for testing different media formulations in parallel was growth of 0.5 ml cultures in 13×100 mm glass culture tubes vertically in a plastic rack in a gyratory incubator at 300-350 rpm. The usual incubation temperature was 37° C., although 20° C. or even lower temperatures were also tested. Time courses of more than a few points were measured in 125-ml Erlenmeyer flasks, usually containing 5 ml or less of medium. These configurations provided sufficient aeration to sustain logarithmic growth to an A600 approaching 10 in the appropriate media. Higher levels of aeration could be achieved with smaller volumes of culture in larger vessels, but the above configurations were used because results obtained with them seemed to translate well to 500 ml culture volumes in 1.8- or 2.8-liter baffled Fernbach flasks, convenient for producing multi-milligram amounts of as many as six proteins at once in a gyratory incubator.

Although they support good growth and protein expression, the usual media are far from optimal. In a typical experiment, saturation density (A600) in ZB was 1.2, in ZY was 2.8, in M9ZB without glucose was 2.6, and in M9ZB containing 2% glucose was 5.8. The usual glucose content of M9ZB is 0.4%, and metabolism of the higher concentration overwhelmed the buffering capacity of M9ZB, producing a final pH of 4.6. Increasing the concentration of N-Z-amine in ZB increased the saturation density approximately in proportion to concentration up to at least 8%, which saturated at A600 of about 8. Adding 1% glucose to 8×ZB or ZY gave little change in saturation density, but greatly reduced the final pH. Increasing the buffering capacity of the medium allowed saturation in glucose-containing media at densities greater than 10. Clearly, even complex media are limited for components needed for growth, and maintenance of a pH near neutral is important for obtaining growth to high density.

To test induction of T7 RNA polymerase in expression hosts in the absence of a target plasmid, the T7 deletion mutant 4107 was used (Studier and Moffatt, *J. Mol. Biol.* 189: 113-130 (1986)). This mutant T7 phage lacks the entire coding sequence for T7 RNA polymerase and is unable to form a plaque on a lawn of cells unless the host cell supplies T7 RNA polymerase. The basal level of T7 RNA polymerase in uninduced BL21 (DE3) is low enough that only small plaques develop at low efficiency, and they typically begin to appear only after about 3 hours. In contrast, induced BL21 (DE3) supports large plaques that become apparent in less than 2 hours, typical of wild-type T7. This 4107 plaque assay was used to test whether T7 polymerase was induced in cultures of BL21(DE3) grown in different media. Cultures grown in media made with the lot of N-Z-amine that did not give induction of target proteins at saturation also appeared uninduced in the plaque assay, giving only small plaques that took a long incubation time develop. Cultures grown in media made with the lot of N-Z-amine that did give induction of target proteins at saturation rapidly gave the large plaques indicative of induction, unless the growth medium also contained glucose, which appeared to prevent induction, as others had reported previously.

Fully defined media were formulated with simple salts and with glucose as the sole carbon source, both to test the requirements for different nutrients and to develop non-inducing media that would support growth of T7 expression strains to saturation at reasonable densities with the lowest possible basal levels of T7 RNA polymerase. When all nutritional requirements are satisfied, the main limitation in achieving high cell densities appears to be maintaining the pH of the culture near neutral, since metabolism of glucose can produce substantial amounts of acid. One solution to this problem is to buffer the medium with phosphate, a required nutrient that buffers in the neutral range. Increasing concentrations of phosphate can buffer the acid generated by higher concentrations of glucose, allowing higher cell densities to be attained while maintaining a pH near neutral (typically greater than pH 6) all the way to saturation. However, too much phosphate can be inhibitory, presumably because of high ionic strength or osmotic pressure. A phosphate concentration of 100 mM seems a reasonable compromise, providing enough buffering capacity to allow growth to saturation in 0.5% glucose while maintaining a pH close to neutrality. Such cultures grow with a doubling time of about 60-70 minutes at 37° C. and saturate at A600 of approximately 5 to 6 and a pH around 6.5. One such growth medium is P0.5G (Table 1).

Several other compounds besides phosphate were tested for ability to help manage the acid produced by the metabolism of glucose or glycerol during growth to saturation. Succinate proved to be particularly useful. Growth of BL21(DE3) on a simple salts medium containing 75 mM succinate (0.23%) as sole carbon source was relatively slow (about a 2 hour doubling time), but the pH of the culture increased with growth (to a pH of 8.7 at an A600 of 0.9). In glucose-succinate mixtures, cultures appear to metabolize glucose preferentially, doubling at about the same rate as in cultures where glucose is the sole carbon source. At appropriate succinate and glucose concentrations, the pH of the growing culture initially decreases and then reverses, presumably as glucose is depleted and succinate is metabolized. For a given medium and culture condition, the range of succinate concentrations that balance the acid generation by glucose, glycerol, or other carbon sources whose metabolism generates acid is easily determined empirically. With too little succinate, the pH at saturation may fall well below 5; with too much succinate the pH at saturation may increase beyond pH 9. In the preferred range of succinate concentrations, the pH at saturation lies between 6.5 and 7.5. A culture grown in a simple salts medium containing 0.5% glucose and 20 mM succinate as sole carbon sources (NIMS medium, Table 1), typically saturates at A600 of approximately 5 to 6, and pH between 6.5 and 7.5. Growth of BL21 (DE3) in simple salts with succinate as sole carbon source did not appear to induce T7 RNA polymerase, as determined by the 4107 plaque assay.

Fumarate and DL-malate are cheap and readily available carbon sources that behave like succinate in their ability to balance acid generation. Citrate and acetate are also effective, but somewhat less so. Growth of BL21 (DE3) in simple salts with succinate as sole carbon source did not appear to induce T7 RNA polymerase, as determined by the 4107 plaque assay. Neither succinate nor any of these other carbon sources, in mixtures with glucose in simple salts media, appear to cause induction of target protein synthesis in T7 expression strains.

Considerable testing of growth of BL21(DE3) or B834 (DE3), with and without target plasmids, showed that all expression strains tested, even strains that express highly toxic target proteins such as the gene 7.7 protein of bacteriophage T7, grow to saturation in P0.5G or NIMS medium with little or no expression of target protein, loss of plasmid, or loss of ability to express plasmid. These media can provide a substantial advantage over typical lots of ZY (or LB) in obtaining expression strains for target proteins that are deleterious to the host. In the case of T7 gene 7.7, transformants in BL21 (DE3) readily gave colonies on P0.5G plates, but no colonies on ZY plates made with the lot of N-Z-amine that caused induction upon approach to saturation.

The ability to balance acid generation with succinate or other carbon sources allows complete flexibility in testing the minimum concentrations of all components (including phosphate) needed for growth of T7 expression strains (or any bacteria) and good expression of target proteins. Tests with P0.5G, NIMS, and media with other combinations of carbon sources (Table 1) showed that minimum concentrations to assure growth to an A600 of at least 5 and good expression of target proteins include approximately 0.5 mM Mg, 5 mM $PO_4$, 25 mM $NH_4$, 0.5 mM $SO_4$, 5-10 μM Fe, and lower concentrations of other metal ions. At least 10 mM Mg, 150 mM $PO_4$, 100 mM $NH_4$, 25 mM $SO_4$, and 500 μM Fe can be tolerated with little or no effect on growth to high density and expression of target proteins. Concentrations in the media that have been tested most extensively have been 1 or 2 mM Mg, 25-100 mM $PO_4$, 25-100 μM $NH_4$, 1-25 mM $SO_4$, and 5-100 μM Fe (Table 1).

Since a significant fraction of proteins bind metals for stability or function, and in structural genomics or other projects the metal-binding properties of target proteins may be unknown, the mixture of trace metal ions given in Table 2 was designed to provide most metal ions that are known to be specifically bound by proteins. A target protein of 50,000 Da produced at a level of 100 mg/liter would have a concentration of 2 μM and a protein of 10,000 Da would have a concentration of 10 μM. The 1× concentration of metal mix provides 2-50 μM of each of 10 different trace ions, probably sufficient to saturate most metal-binding proteins that would be produced. If the metal content of a target protein is known, a saturating amount of that metal can be added specifically. In cultures where target protein is not to be expressed, 0.1× concentration of metal mix should be sufficient for high-density growth, or 50 μM Fe plus 0.02-0.05× metal mix. In cultures whose growth was limited by lack of trace metals, the most dramatic stimulations of growth upon the addition of 1, 10 or 100 μM of individual metal ions of the metal mix were provided by 10-100 μM Fe, 1-100 μM Mn and 1-10 μM Co. Evidence of toxicity up to 100 μM concentration was seen only for Co, which caused a lag before growing well at 10 μM and almost completely prevented growth at 100 μM, and Se, which supported growth normally at 10 μM, but only poorly at 100 μM. At least 5× concentration of metal mix had no apparent deleterious effect on growth to high densities and expression of target proteins in a simple salts medium, and at least 10× metals was tolerated in a simple salts medium plus 200 μg/ml each of 18 of the natural amino acids (no cysteine or tyrosine).

BL21 (DE3) has no nutritional requirements for growth. B834(DE3) was known to require methionine for growth, and 200 μg/ml is sufficient for high density growth and expression of target proteins. In the course of this work, it was discovered that the methionine requirement of B834 could be satisfied instead by vitamin B12 (as little as 1 nM). This demonstrated that B834 is a metE mutant, defective in the vitamin B12-independent homocysteine methylase that would normally synthesize methionine, the last step in methionine biosynthesis. Vitamin B12 is known to activate a second homocysteine methylase of *E. coli*, the product of metH. Since *E. coli* is unable to synthesize vitamin B12, this second enzyme is active only when this vitamin is added to the growth medium. Ability to grow on either methionine or vitamin B12 is the defining characteristic of metE mutants.

To make the media described here generally useful for the growth of expression hosts or other bacteria that may have additional, sometimes multiple nutritional requirements, specific growth factors, mixtures of growth factors such as amino acids, vitamins or nucleosides, or complex media components such as N-Z-amine and yeast extract may be added to the minimal media. Some such media are given in Table 1. A useful stock solution is the mixture of 17 of the 20 natural amino acids, each at 10 mg/ml. Left out of this mixture are cysteine, which slowly forms the essentially insoluble cystine and precipitates; tyrosine, which is only slightly soluble; and methionine, which is often used for radioactive labeling or is replaced by selenomethionine (Se-Met) to label proteins for phasing X-ray crystallographic data. Addition of 18 amino acids (no C or Y) substantially increases the growth rate over that of simple salts media, giving a doubling time of 30-35 minutes as opposed to 60-70 minutes. A concentration of 200 µg/ml of each amino acid seems sufficient for most purposes, although higher concentrations may be better for very high density growths. The omission of cysteine and tyrosine seemed to have little effect on growth rate or saturation density compared to a mixture containing all 20 amino acids. In contrast to amino acids, addition of mixtures of vitamins or nucleosides seemed to give little if any stimulation of the growth rate or increase in saturation density of BL21 (DE3), which has no specific requirement for them. Addition of the complex ZY components to the minimal salts media seemed to provide slightly higher growth rates and saturation densities than the addition of 18 amino acids in most experiments. To minimize the possibility of induction near saturation in complex media, glucose should be added at a high enough concentration that it will not be depleted (as indicated by a decrease in pH and no subsequent increase), typically 0.8% in ZYP medium.

Extensive experience with growing and storing cultures of BL21(DE3) and B834(DE3), alone or containing expression plasmids, in NIMS and in P0.5G indicates that these are excellent media for stable storage of freezer stocks in 8% glycerol at −70° C. or working stocks stored in the refrigerator and used for inoculating subcultures. In contrast to previous experiences with other media, cultures grown to saturation in these media remain viable for periods of weeks to months of storage in the refrigerator, retaining their titer (typically greater than $10^{10}$/ml) and ability to grow subcultures with little or no lag.

2. Development of Auto-Inducing Media

Hoffman et al., *Protein Expression and Purification* 6: 646-654 (1995) reported that fed-batch techniques in a well controlled fermentor allowed induction of target protein synthesis in the T7 system by addition of lactose or glucose-lactose mixtures after depletion of glucose. They proposed that these techniques may slow induction rate and allow more time for proper folding and solubility while producing amounts of protein comparable to those obtained by IPTG induction and culture densities with A600 in the range of 25-40.

It was of interest to determine whether such techniques, when applied to batchwise production of proteins in the T7 expression system in these new media, could increase the solubility of target proteins that were expressed well, but were largely insoluble, of which several were in a structural genomics project. Also, studies of the ClpP protein of *E. coli* had revealed considerable variability in the fraction of soluble ClpP produced, suggesting that lower rates of induction might produce a larger fraction of soluble protein.

The 4107 plaque assay confirmed that growth of BL21 (DE3) to saturation in minimal medium containing 2% α-lactose (and no glucose), with or without added ZY, caused induction of T7 RNA polymerase. However, adding 0.1% or 0.5% lactose to complex medium containing 2% glucose gave only a slight indication of a possible increase in T7 RNA polymerase in the 4107 plaque assay.

Target protein P35 of a structural genomics project (yeast protein coproporphyrinogen III oxidase) under control of a T7lac promoter in a pET vector in B834(DE3) was expressed to substantial levels when grown to saturation in ZYP medium made with the lot of N-Z-amine that showed inducing activity. The protein is apparently not very toxic to the expression host, because the plating efficiency of cells from the saturated culture appeared to be normal. Addition of 1% lactose to the medium produced about a 50% increase in saturation density, but little increase in the level of target protein. However, almost all of the cells capable of forming a colony had lost plasmid. (It was soon discovered that even cells without plasmid can grow quite well in ZYP medium in the presence of 25 µg/ml of kanamycin, the concentration used in this experiment.) Apparently, 1% lactose caused induction to such a high level that cells that contained plasmid were killed. Addition of 0.05% or 0.1% glucose substantially increased the level of target protein produced, apparently by allowing growth to higher density before the level of induction caused by 1% lactose became high enough to kill the cells. Almost all of these surviving cells had also lost plasmid.

These results suggested that perhaps the induction in certain lots of ZYP medium was in fact due to the presence of a small amount of lactose, contrary to what Grossman et al., *Gene* 209: 95-103 (1998) concluded. Their conclusion was based on their finding that β-galactosidase treatment of the medium did not eliminate the induction phenomenon and their inability to detect lactose in the medium (<0.002%). It was tested whether adding lactose to ZYP medium made with the lot of N-Z-amine that showed no inducing activity could reproduce the observed behavior of the lot with inducing activity, namely induction of the target protein to levels readily apparent by gel electrophoresis upon growth to saturation with retention of a typical plating efficiency of cells that essentially all retained plasmid. Indeed, expression was detected by SDS gel electrophoresis with Coomassie blue staining with as little as 0.001% added lactose in the non-inducing medium, and substantial induction was observed at 0.003% lactose or higher. Loss of titer in the saturated cultures started to become significant at 0.01% to 0.02% lactose and was severe by 0.05%. Thus, the lactose concentrations that can cause detectable induction without significant loss of titer are near or below the levels detectable by Grossman et al., *Gene* 209: 95-103 (1998).

It was concluded that, contrary to the belief in the previous art, the presence of small amounts of lactose in some commercial lots of complex media is an important factor, and perhaps the determining factor, in the spontaneous induction of target protein synthesis sometimes observed in the T7 expression system near the onset of stationary phase. The conclusion seems quite reasonable given that the complex media contain tryptic digests of casein (a milk protein), milk contains substantial amounts of lactose, and only very small amounts of lactose are needed to cause induction. Although the casein used in the tryptic digests was purified in its preparation from milk, it seems almost certain that small amounts of lactose contaminating certain lots of purified casein are responsible for the inducing activity observed.

The realization that the inducing activity was due to lactose, together with the results of experiments exploring the effects of different mixtures of glucose and lactose on induction behavior, caused rethinking of the results and conclusions of Hoffman et al., *Protein Expression and Purification* 6: 646-654 (1995) on the induction of target protein by batch-fed lactose or glucose-lactose mixtures under controlled conditions in a fermentor.

It seemed from initial results that cultures grown in different mixtures of glucose and lactose were not inducing production of target protein at intermediate rates, as proposed by Hoffman et al., *Protein Expression and Purification* 6: 646-654 (1995), but were in fact growing with little or no induction until the glucose was depleted, and only then being induced by the lactose present in the medium. A comprehensive series of tests, including time courses of growth and induction under different conditions, were consistent with this interpretation. The term auto-induction is used to refer to the growth pattern of inducible expression strains in inducer-containing media, where growth is essentially normal in the early stages, with little or no induction, and expression of the target protein is turned on automatically at a later stage of growth, with no intervention. Much of the testing to define the auto-induction behavior and the factors affecting it was done with target protein P21 of a structural genomics project, a well induced, not particularly toxic protein (yeast peptide chain release factor subunit 1) expressed under control of a T7lac promoter in a pET vector in B834(DE3) which also contained a compatible plasmid expressing tRNAs for rare arginine, isoleucine and leucine codons. The results may be summarized as follows.

Little growth was apparent in simple salts media containing lactose as sole carbon source, presumably because the level of induction was too high to allow growth. Addition of increasing concentrations of glucose to media containing 0.1% to 1.5% lactose allowed growth to increasing saturation densities, with expression of target protein occurring in cultures that had low glucose concentrations, but decreasing to undetectable levels at about 0.5% glucose or higher. In somewhat of a surprise, ZY-containing media with no added glucose suppressed induction by even high concentrations of lactose (1.5%) to undetectable levels during early log phase growth, followed by high-level induction of target protein, typically occurring at an A600 between about 1 and 2. This suppression of induction by lactose in early log phase in the absence of added glucose is apparently due, at least partly, to the presence of amino acids rather than, for example, contaminating glucose in the complex ZY media, because purified amino acids also have this suppressive effect in simple salts media containing lactose and glycerol. Serine seems to be particularly effective in suppressing lactose induction in early log phase, and can itself allow growth and induction in a lactose-glycerol mixture about as well as a mixture of all 20 amino acids. Serine is not required, however, as a mixture of 17 amino acids lacking serine, cysteine and tyrosine was also effective.

Lactose itself appears not to be a very good carbon source for growth of auto-induced cultures to high cell densities. Addition of glycerol to simple or complex media allows growth to much higher densities and does not seem to interfere with auto-induction. Mixtures containing from 0.5% to 2.5% glycerol with 0.05% glucose and 0.2% lactose have been very effective at promoting growth to high culture densities and auto-induction of many different target proteins in both simple and complex media. A short-hand notation for these particular mixtures has been 5052 to designate the mixture 0.5% glycerol, 0.05% glucose, 0.2% lactose, 10052 to designate 1% glycerol, 0.05% glucose, 0.2% lactose, and so on, where the last three digits, 052, denote the 0.05% glucose, 0.2% lactose and the first one or two digits refer to the concentration of glycerol. Other economical and readily available carbon sources that have been effective in promoting high-density growth and auto-induction in combination with glucose and lactose include maltose and sorbitol.

Saturation densities of auto-induced cultures can vary considerably depending on the effect of the expressed target protein on the host cell. Auto-induced cultures which express target proteins that directly affect growth may saturate with high levels of target protein at an A600 of around 5. More typical are saturation densities in an A600 range of 10-20, and densities as high as 30-50 have been observed. Auto-induction with production of large amounts of target protein has been effective with many different target proteins at temperatures between 18° C. and 37° C.

One factor that significantly affects the saturation density is level of aeration. This was varied in experiments by changing the volume of culture relative to the volume of the vessel. Lower relative volumes of culture provide higher levels of aeration. Both saturation and induction occurred at lower cell density, the lower the level of aeration, but the level of target protein produced per cell seemed to remain fairly constant over a range of saturation densities. Extremely high aeration occasionally seemed to delay or reduce induction to the point where it hardly occurred, perhaps because an extremely high cell density depleted an essential nutrient, or because some general stress response involved in high-level induction was muted. Growth of 0.5-ml cultures in 13×100 mm glass culture tubes or 500-ml cultures in 2- or 2.8-liter baffled Fernbach flasks seem to provide an appropriate level of aeration for effective auto-induction with media formulations comparable to those given in Table 1.

The auto-induction phenomenon is consistent with a large body of previous work showing that the presence of glucose in the growth medium excludes the use of lactose both by preventing the uptake of lactose from the medium by the lac permease, and through catabolite repression, which operates through the effect of glucose metabolism on cAMP levels. However, the lacUV5 promoter, which directs the expression of T7 RNA polymerase, does not require cAMP-mediated activation and can be induced by IPTG in the presence of glucose. IPTG acts directly as an inducer and does not require the lac permease to enter the cell. Induction by lactose, on the other hand, requires both uptake by the lac permease, and conversion to the true inducer by the transgalactosidation activity of β-galactosidase. Thus, one would not expect auto-induction to work in T7 expression strains that carry mutations in the lac permease because such cells cannot take up lactose, nor in cells that carry mutations in β-galactosidase that prevent the transgalactosidation reaction which generates the true repressor.

Grossman et al., *Gene* 209: 95-103 (1998) found that unintended induction was reduced in a cAMP-deficient mutant of BL21 (DE3), and proposed that cAMP, rather than acting directly on the lac promoter, may trigger a general stress response occurring during the approach to saturation. It seems quite possible that some such response may be involved in the auto-induction phenomenon.

Catabolite repression and inducer exclusion by the presence of glucose in the growth medium is a general phenomenon in *E. coli* and is known to affect other carbon sources besides lactose, including galactose, maltose, arabinose, and many others. Expression systems that use promoters regulated by any of the compounds subject to catabolite repression and inducer exclusion would also be suitable for application of the auto-induction methods disclosed here.

3. Applications

The current understanding of auto-induction of target protein production in the T7 system, and the development of reliable media and protocols for batchwise growth of expression strains to saturation either with essentially no induction or with auto-induction of high levels of target protein at high culture densities, has great utility for producing proteins from cloned coding sequences. Both non-inducing and auto-inducing cultures are simply inoculated and grown to saturation. Non-inducing media produce cultures that are viable for weeks at refrigerator temperature for making subcultures for screening expression and solubility or production of substantial amounts of target protein. Agar plates made with non-inducing media also allow expression strains to be obtained for some target proteins that are too toxic to be obtained in typical commercial media.

In contrast to conventional inductions by addition of either IPTG or lactose, where growth of each culture must be monitored and inducer (IPTG or lactose) added at the proper time, auto-inducing cultures are simply inoculated and grown to saturation. At 37° C., high-level auto-induction is usually achieved in 14 hours in minimal salts media, or 8-10 hours in media supplemented with ZY or amino-acid mixtures, convenient lengths of time for overnight inductions. Continued incubation for several hours after saturation appears not to be deleterious. In fact, where high levels (typically 2% or more) of glycerol or other neutral carbon source such as maltose are present and the pH remains near neutral, cell density can continue increasing slowly for 24 hours or longer and can lead to substantial further increases in culture density and yield of target protein. (A potential problem with using high concentrations of maltose is that most lots have significant contamination with glucose, which, if high enough, could interfere with induction.) Auto-induction at lower temperatures, such as 20° C. requires substantially longer incubations, often 24-36 hours. The incubation time can be shortened without reducing the desired solubility of the induced target protein by incubating the cultures at 37° C. for a few hours and then transferring them to the lower temperature before they become more than lightly turbid.

The densities of induced cells obtained by auto-induction in the disclosed media are much higher than those typically produced by conventional induction. The densities of batchwise auto-induced cultures are typically high enough that screening for expression and solubility is accomplished with 5-50 μl of culture, readily obtainable in 96-well plates. The simplicity and reliability of obtaining non-induced and auto-induced cultures makes highly parallel screening of many target proteins readily automatable.

Larger-scale growth of auto-induced cultures to obtain protein for purification is readily accomplished in baffled flasks on a rotory incubator at 300-350 rpm. A single 1.8- or 2.8-liter baffled Fernbach flask with 500 ml of auto-induced culture can yield tens to hundreds of milligrams of target proteins from well expressed clones, sufficient for structure determination and many other purposes. It is not unusual for auto-induced cultures to yield ten times the amount of purified target protein as obtained from the same volume of culture induced with IPTG in the conventional way.

The disclosed fully defined auto-inducing media also make it possible to develop media for efficiently labeling proteins. Useful examples are Se-Met labeling for protein structure determination by X-ray crystallography, or isotopic labeling for structure determination by NMR. An efficient auto-inducing medium for Se-Met labeling is the PASM-5052 medium given in Table 1.

To label target proteins with Se-Met, PASM-5052 medium is inoculated with a fresh overnight culture grown in PA-0.5G. Growth at 37° C. from a thousand-fold dilution into PASM-5052 typically reaches saturation in 14-16 hours. Growth at 20° C. is much slower and a culture can take 3 days or longer to become induced and reach saturation.

Auto-induction in PASM-5052 medium will produce target proteins essentially fully labeled with Se-Met when expressed in either the methionine auxotroph B834(DE3) or the prototroph BL21 (DE3). The presence of Se-Met reduces the growth rate of the two strains comparably, presumably because both strains incorporate Se-Met into their proteins in place of methionine (but possibly due to other toxic effects as well). Enzymes of the methionine synthesizing pathway are apparently repressed by the presence of Se-Met in the medium, as they would be by methionine, preventing endogenous production of methionine.

The small amount of methionine present in PASM-5052 medium allows significantly faster growth in the presence of Se-Met, and the concentration of Se-Met is sufficient to support the growth of the methionine-requiring B834 to saturation (in the absence of vitamin B12). The presence of vitamin B12 in PASM-5052 medium significantly increases the yield of target protein and largely prevents the appearance of a brown-orange color that can appear in cells upon continued incubation at saturation in the presence of a slight excess of Se-Met. Vitamin B12 is known to activate an enzyme (the product of metH) that methylates homocysteine to produce methionine. Perhaps a significant fraction of Se-Met is converted to Se-homocysteine during growth or induction in this medium, and the B12-dependent methylase stimulates production of target protein by regenerating Se-Met.

TABLE 1

Compositions of representative non-inducing and auto-inducing media

| | $Na_2HPO_4$ mM | $KH_2PO_4$ mM | $NH_4Cl$ mM | $(NH_4)_2SO_4$ mM | $Na_2SO_4$ mM | $MgSO_4$ mM | $FeCl_3$ μM | metl | 18aa ZY μg/ml | Glyc % | Gluc % | Lact % | Succ mM |
|---|---|---|---|---|---|---|---|---|---|---|---|---|---|
| Non-inducing media: | | | | | | | | | | | | | |
| P-0.5G | 50 | 50 | | 25 | | 1 | 0.1x | | | | 0.5 | | |
| PA-0.5G | 50 | 50 | | 25 | | 1 | 0.1x | 100 | | | 0.5 | | |
| ZYP-0.8G | 50 | 50 | | 25 | | 1 | | | 1x | | 0.8 | | |
| NIMS | 12.5 | 12.5 | 50 | | 5 | 1 | 0.1x | | | | 0.5 | | 20 |

TABLE 1-continued

Compositions of representative non-inducing and auto-inducing media

| | Na$_2$HPO$_4$ mM | KH$_2$PO$_4$ mM | NH$_4$Cl mM | (NH$_4$)$_2$SO$_4$ mM | Na$_2$SO$_4$ mM | MgSO$_4$ mM | FeCl$_3$ μM | metl | ZY | 18aa μg/ml | Glyc % | Gluc % | Lact % | Succ mM |
|---|---|---|---|---|---|---|---|---|---|---|---|---|---|---|
| Auto-inducing media: | | | | | | | | | | | | | | |
| ZYP-5052 | 50 | 50 | | 25 | | 1 | | 1x | 1x | | 0.5 | 0.05 | 0.2 | |
| PA-5052 | 50 | 50 | | 25 | | 1 | | 1x | | 200 | 0.5 | 0.05 | 0.2 | |
| P-5052 | 50 | 50 | | 25 | | 1 | | 1x | | | 0.5 | 0.05 | 0.2 | |
| PASM-5052 | 50 | 50 | | 25 | | 1 | | 1x | | ** | 0.5 | 0.05 | 0.2 | |
| MS-15052 | 12.5 | 12.5 | 50 | | 5 | 2 | 50 | 1x | | | 1.5 | 0.05 | 0.2 | 35 |
| MAS-15052 | 12.5 | 12.5 | 50 | | 5 | 2 | 50 | 1x | | 200 | 1.5 | 0.05 | 0.2 | 15 |
| ZYM-15052 | 12.5 | 12.5 | 50 | | 5 | 2 | 50 | 1x | 1x | | 1.5 | 0.05 | 0.2 | |

** PASM-5052 contains 200 μg/ml each of 17 amino acids (no M, C, Y), 10 μg/ml methionine, and 125 μg/ml selenomethionine plus 100 nM of vitamin B12
ZY is 1% N-Z-Amine AS + 0.5% yeast extract
metl is the metals mix shown in Table 2
Metals may be omitted from media containing ZY if high concentrations are not required
Metals may be reduced to 0.1x in simple salts media if high concentrations are not required
18aa gives the concentration of each of 18 of the natural amino acids (no cysteine or tyrosine)
Glyc is glycerol
Gluc is glucose
Lact is alpha lactose
Succ is Na$_2$ succinate

TABLE 2

Composition of a Trace Metals Mix (1x)

50 μM FeCl$_3$
20 μM CaCl$_2$
10 μM MnCl$_2$
10 μM ZnSO$_4$
2 μM CoCl$_2$
2 μM CuCl$_2$
2 μM NiCl$_2$
2 μM Na$_2$MoO$_4$
2 μM Na$_2$SeO$_3$
2 μM H$_3$BO$_3$

Dilute from a 1000x stock solution in ~50 mM HCl

The invention claimed is:

1. A bacterial growth medium for promoting auto-induction, in bacterial cells grown batchwise, of expression from a promoter which is repressed by a lac repressor, which medium is selected from the group consisting of ZYP-5052, PA-5052, P-5052, PASM-5052, MAS-15052, MS-15052, ZYM-15052 and combinations thereof.

2. The bacterial growth medium of claim 1 wherein the promoter is selected from the group consisting of a lac promoter, a lacUV5 promoter and a T7lac promoter.

3. The bacterial growth medium of claim 1 wherein the auto-induction results in expression of a cloned gene 1 of bacteriophage T7, which gene is adapted for stable propagation in said cells, resulting in production of a gene 1 gene product.

4. The bacterial growth medium of claim 3 wherein the bacterial cells contain a DE3 lysogen or derivative thereof.

5. The bacterial growth medium of claim 4 wherein the bacterial cells are selected from the group consisting of Escherichia coli, Bacillus subtilis, Ralstonia eutrophus, Salmonella enterica serovar Typhimurium, Pseudomonads and Rhodobacter capsulatus.

6. The bacterial growth medium of claim 5 wherein the cells are Escherichia coli.

7. The bacterial growth medium of claim 6 wherein the E. coli cells are selected from the group consisting of BL21 (DE3), B834(DE3), HMS174(DE3), and derivatives thereof.

8. The bacterial growth medium of claim 3 wherein the bacterial cells further contain a target DNA in a T7 plasmid expression vector, which target DNA optionally comprises a coding sequence for a target protein.

9. The bacterial growth medium of claim 8 wherein transcription of the target DNA is additionally controlled by the lac repressor.

10. The bacterial growth medium of claim 8 wherein the auto-induced gene 1 gene product transcribes the target DNA.

11. The bacterial growth medium of claim 9 wherein the auto-induced gene 1 gene product transcribes the target DNA.

12. The bacterial growth medium of claim 11 wherein the transcripts of the target DNA are translated into the target protein.

13. A bacterial growth medium for promoting auto-induction, in bacterial cells grown batchwise, of expression from a promoter which is repressed by a lac repressor, comprising ZYP-5052, PA-5052, P-5052, PASM-5052, MAS-15052, MS-15052, ZYM-15052 or combinations thereof.

14. The bacterial growth medium of claim 1, excluding PASM-5052, further comprising vitamin B12 and about 75 μg/ml to about 150 μg/ml Seleno-methionine and wherein the bacterial cells encode a vitamin B12-dependent homocysteine methylase.

15. The bacterial growth medium of claim 1 comprising PASM-5052 wherein the bacterial cells encode a vitamin B12-dependent homocysteine methylase.

* * * * *